United States Patent [19]

Okuzumi

[11] 4,017,463
[45] Apr. 12, 1977

[54] HIGH MELTING N,N-TEREPHTHALOYL BIS-PHTHALIMIDE AND ITS USE AS AN ESTER INTERLINKING AGENT FOR POLYESTERS

[75] Inventor: Yuzi Okuzumi, Cuyahoga Falls, Ohio

[73] Assignee: The Goodyear Tire & Rubber Company, Akron, Ohio

[22] Filed: July 21, 1975

[21] Appl. No.: 597,795

Related U.S. Application Data

[63] Continuation of Ser. No. 465,215, April 29, 1974.

[52] U.S. Cl. .......................... 260/75 T; 260/75 N; 260/326 N; 260/326 A
[51] Int. Cl.$^2$ .................. C08G 63/46; C08G 63/68
[58] Field of Search ............ 260/75 T, 75 N, 75 M

[56] References Cited

UNITED STATES PATENTS

| | | |
|---|---|---|
| 2,558,675 | 6/1951 | Flory ............................. 260/326 N |
| 2,594,145 | 4/1952 | Flory ............................. 260/75 T |
| 3,444,141 | 5/1969 | Shima ............................ 260/75 T |
| 3,714,125 | 1/1973 | Shima et al. .................... 260/75 M |
| 3,776,882 | 12/1973 | Witzler et al. ................ 260/45.9 DI |
| 3,803,099 | 4/1974 | Okuzumi ........................ 260/75 M |

Primary Examiner—Howard E. Schain
Assistant Examiner—W. C. Danison, Jr.
Attorney, Agent, or Firm—F. W. Brunner; J. M. Wallace, Jr.

[57] ABSTRACT

There is disclosed, as a composition of matter, a new, high melting N,N'-terephthaloyl bis-phthalimide, a method for its preparation employing as a solvent a high boiling aromatic or aliphatic-aromatic ether or a mixture of a high boiling aromatic or aliphatic-aromatic ether and a low boiling cyclic or aliphatic ether and the use of said new, high melting N,N'-terephthaloyl bis phthalimide as an ester interlinking agent for polyester.

6 Claims, No Drawings

HIGH MELTING N,N-TEREPHTHALOYL BIS-PHTHALIMIDE AND ITS USE AS AN ESTER INTERLINKING AGENT FOR POLYESTERS

This is a continuation of application Ser. No. 465,215, filed Apr. 29, 1974.

This invention relates to N,N'-terephthaloyl bis-phthalimide. More particularly the invention relates to a method of preparing N,N'-terephthaloyl bis-phthalimide having a high melting point, to its use as an interlinking agent in the preparation of high molecular weight polyesters and copolyesters and to fibers and other molded products thereof.

U.S. Pat. No. 2,558,675 discloses the preparation of polyimide derivatives of carboxylic acids by the condensation of an acid imide (preferably in the form of an alkali metal salt) with a polyacyl chloride or polyacyl bromide of a carboxylic acid. This prior art patent, as well as U.S. Pat. No. 2,594,145, further discloses that said derivatives find utility in the preparation of highly polymeric materials by using the derivatives to join or interlink molecules of moderate molecular weight. An attempt was made to repeat the teachings of U.S. Pat. No. 2,558,675, particularly with respect to the preparation and use of N,N'-terephthaloyl bis-phthalimide. The procedure set forth in Example 5 (see Column 4, lines 4-15) of the above cited patent was followed as closely as possible. There was obtained a product having a melting point (270°- 275° C. with decomposition) corresponding to that reported for the product in Example 5 of the above noted patent. Unexpectedly, however, and contrary to the disclosure of the patent, this product, when added to a melted sample of polyester caused no interlinking of the chain ends. In fact, the polyester sample actually underwent a reduction in molecular weight as evidenced by a decrease in its original intrinsic viscosity. Repeated attempts at using recrystallized samples of the product failed to provide any different result. Thus it was found that the product prepared according to the teachings of Example 5 of U.S. Pat. No. 2,558,675 does not promote the ester interlinking reaction of polyester chains.

Now, in contrast to the teaching of U.S. Pat. No. 2,558,675, it has been found that when a mixture of terephthaloyl chloride and an imide compound selected from phthalimide and alkali metal salts of phthalimide such as lithium phthalimide, sodium phthalimide, potassium phthalimide and the like are reacted in high boiling aromatic or aliphatic-aromatic ethers or mixtures comprising a high boiling aromatic or aliphatic-aromatic ether component and a low boiling cyclic or aliphatic ether component the product has a melting point of at least 330° C. Furthermore, this product has ester interlinking properties and is effective in increasing the polymerization rate of polyester forming reactants as well as increasing the molecular weight of condensation polyesters.

In order to prepare the new high melting N,N'-terephthaloyl bis-phthalimide described herein in good yield the reaction between the terephthaloyl chloride and the phthalimide or alkali metal salt thereof is carried out at temperatures ranging from 70° to 170° C. in the initial stages of the reaction and at temperatures ranging from 200° to 400° C. in the final stages of the reaction.

Preferably these conditions are accomplished through the use of a solvent medium consisting initially of a mixture of a high boiling ether component selected from the group consisting of aromatic and aliphatic-aromatic ethers and a low boiling ether component selected from the group consisting of aliphatic and cyclic ethers. The high and low boiling ether components are selected such that during the initial reaction stages (i.e., the first 0.5 – 5.0 hours) in the preparation of the high melting N,N'-terephthaloyl bis-phthalimide the temperature of reaction will fall within the above specified 70°– 170° C. range. As the reaction proceeds the low boiling ether component is slowly distilled out of the reaction mixture and the preparation continued to completion at a temperature between 200°– 400° C. and preferably at the boiling point of the high boiling ether component. Given the respective boiling points of any particular high boiling and low boiling ether one of ordinary skill in the art can readily determine the amounts of each which will be needed to produce a solvent mixture to provide an initial reaction temperature within the limits specified above. For example, in the preparation of high melting N,N'-terephthaloyl bis-phthalimide described in Example 1 below the solvent mixture employed consisted of diphenyl ether having a boiling point of 254° C. and dioxane having a boiling point of 101° C. It was readily determinable that a 50/50 volume mixture of these two ethers would provide for a reaction temperature between the prescribed 70° – 170° C. range. The actual boiling point of the mixture was observed to range from 110°– 115° C.

The high melting N,N'-terephthaloyl bis-phthalimide of this invention can also be prepared employing the high boiling ethers, described hereinbelow, as the sole solvent medium. Again, as with the use of the mixed solvent system, the initial stages of the reaction, i.e., the first 0.5 to 5.0 hours of the reaction, are carried out at temperatures ranging from 70° to 170° C. For the final stages of the reaction the temperature is raised to between 200° and 400° C. and preferably to the boiling point of the high boiling ether solvent to complete the reaction. Failure to observe the above temperature conditions, and particularly the initial temperature conditions when employing a high boiling ether as the sole solvent medium, will lead to poor conversions due to volatilization of the terephthaloyl chloride reactant.

By the term "high boiling" ether component is meant those aromatic and aliphatic aromatic ethers having boiling points ranging from 200° to 400° C. and melting points below 50° C. and preferably below 30° C. While it is most convenient to employ high boiling ethers which are liquids at ambient temperatures the most preferred high boiling ether, diphenyl ether, is a solid at ambient temperatures which must be melted prior to use. By the term "low boiling" ether component is meant those aliphatic and cyclic ethers having boiling points between 65° and 150° C.

In addition to diphenyl ether, other examples of useful high boiling ethers include benzyl butyl ether, butyl phenyl ether, isoamyl phenyl ether, hexylphenyl ether, heptylphenyl ether, octylphenyl ether, propyl tolyl ether, butyl tolyl ether, methyl naphthyl ether, ethyl naphthyl ether, propyl naphthyl ether and the like. Examples of useful low boiling ethers, in addition to dioxane, include isopropyl ether, ethyl isobutyl ether, ethyl isoamyl ether, isobutyl ether, ethylhexyl ether, butyl ether, tetrahydrofuran, tetrahydropyran and the like.

According to the preferred procedure for preparing the high melting N,N'-terephthaloyl bis-phthalimide disclosed herein, terephthaloyl chloride and potassium phthalimide are reacted in a mixed solvent system consisting of 50 percent by volume diphenyl ether and 50 percent by volume of dioxane. Employment of this particular mixed solvent system provides reaction temperatures between 110° to 115° C. during the initial one to two hours of the preparation. During the course of the reaction and after the initial 1 to 2 hours of reaction time the dioxane is gradually distilled from the reaction mixture and the reaction completed at the boiling point of the diphenyl ether over an additional 1 to 2 hour period. Thus, during the course of the preparation the reaction temperature ranges from about 110° C. to 254° C. At the end of this time the reaction mixture is filtered to remove the potassium chloride by-product and then cooled and the N,N'-terephthaloyl bis-phthalimide precipitating from the diphenyl ether at temperatures down to 60° C. collected and dried.

The following examples illustrate the invention. In these examples all parts and percentages are by weight unless otherwise indicated. "I.V." stands for intrinsic viscosity as measured in a 60/40 phenol/tetrachloroethane mixed solvent at 30° C. and is a measure of the molecular weight of the polyester.

EXAMPLE 1

The apparatus employed to prepare the high melting N,N'-terephthaloyl bis-phthalimide consists of a 2000 milliliter (ml.) glass reaction vessel equipped with a stirrer, thermometer, condenser, nitrogen inlet and a valved outlet located at the bottom of the reaction vessel. The glass reaction vessel was compartmentized by a sintered glass partition which was located immediately above the valved outlet. The reaction vessel was attached to a receiving flask, equipped with a vacuum outlet, through the valved outlet. To this reaction vessel were added 37.4 grams (0.203 mol) of potassium phthalimide in a mixture of 250 ml. of dioxane and 500 ml. of diphenyl ether. Then 20.3 grams (0.1 mol) of terephthaloyl chloride were dissolved in 250 ml. of dioxane and this mixture slowly added to the reaction vessel with constant stirring. The contents of the reaction vessel were gradually heated to reflux temperature (between 110° to 115° C.) and maintained at reflux for 1 hour. At the end of this time the dioxane solvent component was slowly distilled from the reaction mixture through a fractional distillation column. After the dioxane was completely removed the reaction mixture was maintained at the boiling point of the diphenyl ether (about 254° C.) for an additional 1 hour. The hot solution, containing suspended potassium chloride by-product, was then quickly filtered, at the boil and under vacuum, into the receiving flask. White crystals of N,N'-terephthaloyl bis-phthalimide (TBP) product immediately formed in the filtrate. When the filtrate had cooled to about 100° C. the white crystals were collected by filtration and dried under heat and vacuum. The dried crystals [Product (I)] weighed 36.5 grams, representing a yield of 87.3 percent and had a melting point of 340° to 345° C. As the filtrate cooled to about 60° C. more white crystals formed which were collected and dried under heat and vacuum. These crystals [Product (II)] had a melting point of 330° to 336° C. The precipitate collected below 60° C. [Product (III)] was also dried under heat and vacuum and its melting point found to be 315° to 325° C. A portion of Product (I) was recrystallized from diphenyl ether. The recrystallized material had a melting point of 354° to 357° C. A portion of this recrystallized material was then again recrystallized from diphenyl ether and the melting point of the material found to be 365° to 367° C. An analysis of this latter material gave 68.06 percent carbon, 2.85 percent hydrogen and 6.35 percent nitrogen. The calculated values for the compound having the above formula are 67.93 percent carbon, 2.85 percent hydrogen and 6.60 percent nitrogen.

In view of the above analysis the product is believed to have the structure

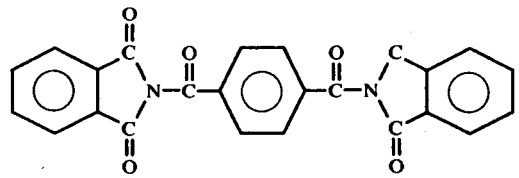

which has the chemical name N,N'-terephthaloyl bis-phthalimide. For convenience, in this specification this is abbreviated and referred to hereinafter as TBP.

A widely employed method of increasing the rate of polycondensation in polyester forming processes is by the addition of a reactive material capable of interlinking polymer chains. Such ester interlinking materials provide efficient and economical means for producing polymers of high molecular weight. In the preparation of poly(ethylene terephthalate), for example, the use of aromatic ortho carbonates (U.S. Pat. No. 3,714,125), carbonate derivatives of monovalent phenols (U.S. Pat. No. 3,444,141) and diaryl esters of dicarboxylic acids (U.S. Pat. No. 3,433,770) are but a few of the materials that have been employed to increase the rate of polycondensation to provide a high molecular weight polyester in shorter than normal condensation reaction times. The development of a new interlinking material is an important contribution to this field. The new product was tested and found to be an effective interlinking agent.

The utility of the new high melting interlinking agent is shown in the examples below.

EXAMPLES 2 – 5

In each of Examples 2 through 5 a glass reaction tube approximately 35 centimeters long having an inside diameter of 38 millimeters, equipped with a side arm, a nitrogen gas inlet tube and stirrer was charged with 50 grams of dimethyl terephthalate, 40 grams of ethylene glycol and 0.01 percent (calculated as metal) of manganese octoate. Nitrogen gas was slowly passed into the reaction tube and over the mixtures. The mixture was stirred and heated by means of a vapor bath, which surrounded the tube, having a temperature of 240° C. After completion of the transesterification reaction, polycondensation was commenced by adding 0.0123 gram (calculated as metal) of antimony trioxide, increasing the temperature of the mixture to 280° C. and gradually reducing the pressure in the tube to 0.05 millimeter of mercury pressure. In Examples 2 and 3 the polycondensation reactions were carried out for 50 minutes and the mixtures sampled to determine their intrinsic viscosities (I.V.) at that point. Varying amounts of the twice recrystallized TBP of Example 1 were then added to these mixtures and the polycondensation reactions continued for an additional 2 minutes. Examples 4 and 5 were carried out in the same manner except that the polycondensation reaction was run for 65 minutes before sampling and addition of the twice recrystallized TBP prepared in Example 1. All pertinent data in each instance were noted and recorded. These data are set forth in Table I.

TABLE I

| Example No. | Polycondensation Time, Minutes | Original I.V. | Amount of TBP Added[a] | Final I.V. |
|---|---|---|---|---|
| 2 | 50 | 0.509 | 1.40 | 0.735 |
| 3 | 50 | 0.509 | 1.96 | 0.817 |
| 4 | 65 | 0.592 | 1.10 | 0.908 |
| 5 | 65 | 0.592 | 1.54 | 0.926 |

[a]Parts by weight per 100 parts by weight of dimethyl terephthalate.

EXAMPLE 6

Employing the same apparatus, materials and amounts thereof as in any of Examples 2 through 5 a comparative example was run in which no high melting TBP was added in order to illustrate the normal polycondensation rate. During the polycondensation reaction samples were withdrawn every 10 minutes. The results are set forth in Table II.

TABLE II

| Sample No. | Polycondensation Time, Minutes | I.V. |
|---|---|---|
| 1 | 40 | 0.435 |
| 2 | 50 | 0.509 |
| 3 | 60 | 0.565 |
| 4 | 70 | 0.621 |
| 5 | 80 | 0.666 |
| 6 | 90 | 0.703 |
| 7 | 100 | 0.735 |
| 8 | 110 | 0.754 |
| 9 | 120 | 0.762 |

From a comparison of Tables I and II it is apparent that the addition of small amounts of pure TBP greatly accelerates the polycondensation rate over that of the normal polycondensation reaction rate.

EXAMPLES 7 – 12

In each of examples 7 – 12, 50 grams of poly(ethylene terephthalate) having an I.V. of 0.809 were charged to a glass reaction tube approximately 35 centimeters long having an inside diameter of 38 millimeters and equipped with a side arm, nitrogen gas inlet tube and stainless steel stirrer. In each of the examples the poly(ethylene terephthalate) was melted at 280° C. under a nitrogen atmosphere. To each of Examples 8 – 12 were added 0.5 part by weight of one of the TBP products from Example 1 per 100 parts by weight of polyester. The mixtures were stirred at constant speed, at 280° C. and under nitrogen atmosphere for five minutes and then discharged. The I.V. of each of the polymer samples was again determined. The results from these experiments are listed in Table III. These results demonstrate that only TBP having a melting point of at least 330° C. possesses the ability to interlink polyester chain ends and that the higher the purity the greater this ability. These examples also demonstrate the ability of high melting TBP to cause further polymerization of high I.V. polyester under melt polymerization conditions, a feat which normally would have to be carried out under solid state polymerization conditions.

TABLE III

| Example No. | Original I.V. | M.P. of TBP Added, ° C. | Final I.V. |
|---|---|---|---|
| 7[a] | 0.809 | — | 0.809 |
| 8 | 0.809 | 315–325 | 0.807 |
| 9 | 0.809 | 330–336 | 0.828 |
| 10 | 0.809 | 340–345 | 0.899 |
| 11 | 0.809 | 354–357 | 0.959 |
| 12 | 0.809 | 365–367 | 1.051 |

[a]Control

It should be noted that TBP having a melting point below 330° C., surprisingly, causes a decrease in the original I.V. of polyester as evidenced by the result obtained in Example No. 8.

EXAMPLES 13 – 15

In each of Examples 13 through 15, 30 pound quantities of commercial poly(ethylene terephthalate) chips having an I.V. of 0.972 were added to a 3-cubic foot blender-dryer and tumbled for 2 hours at 150° C. under 0.1 millimeter of mercury vacuum. In addition, Example 14 contained 0.4 part by weight of the twice recrystallized TBP samples from Example 1 per 100 parts by weight of polyester and Example 15 contain 0.4 part of a TBP sample prepared in accordance with the teachings of U.S. Pat. No. 2,558,675 (Example 5) per 100 parts by weight of polyester. Employing a 1-inch extruder, the three samples were then separately extruded into fibers. The residence time of the resin in the extruder was approximately 1 minute. All pertinent physical data are listed in Table IV below.

TABLE IV

| Example | Original I.V. | Fiber I.V. | Fiber M.P. ° C. | Loss in I.V. % |
|---|---|---|---|---|
| 13 | 0.972 | 0.847 | 258.0 | 12.9 |
| 14 | 0.972 | 0.965 | 257.5 | 0.7 |
| 15 | 0.972 | 0.811 | 257.0 | 16.6 |

From Example 14 it can be seen that the high melting TBP of the present invention functions most effectively to essentially retain in the fiber the high molecular weight of the polyester feed resin, whereas the prior art TBP does not. And again, it was most surprising that the poly(ethylene terephthalate) sample containing the prior art TBP (Example 15) experienced a greater loss in I.V. than the sample in which no TBP had been added.

EXAMPLES 16 – 24

The procedure employed in Examples 13 – 15 was repeated in Examples 16 – 24 employing varying amounts of the twice recrystallized TBP from Example 1 and poly(ethylene terephthalate) resin of varying initial intrinsic viscosities. Employing a 1-inch extruder, all samples were separately extruded into fibers. All pertinent data are listed in Table V below.

TABLE V

| Example No. | Resin I.V. | Amount of TBP Added[a] | Fiber I.V. | Fiber[c] Tenacity g/d |
|---|---|---|---|---|
| 16[b] | 0.592 | 0 | 0.502 | — |
| 17 | 0.592 | 0.5 | 0.657 | — |
| 18 | 0.592 | 1.0 | 0.738 | — |
| 19 | 0.592 | 1.5 | 0.770 | — |
| 20 | 0.592 | 2.0 | 0.790 | — |

TABLE V-continued

| Example No. | Resin I.V. | Amount of TBP Added[a] | Fiber I.V. | Fiber[c] Tenacity g/d |
|---|---|---|---|---|
| 21[b] | 0.627 | 0 | 0.583 | 6.07 |
| 22 | 0.627 | 1.5 | 0.806 | 7.90 |
| 23[b] | 0.759 | 0 | 0.689 | 6.78 |
| 24 | 0.759 | 0.8 | 0.939 | 8.32 |

[a]Parts by weight TBP per 100 parts by weight of polyester
[b]Controls wherein no TBP was blended with the polyester
[c]g/d - grams per denier The above examples illustrate the ability of the high melting TBP to produce fibers of higher I.V. than the resin from which they were formed. In the absence of the high melting TBP the fibers exhibit a lower I.V. than the starting resin. This decrease in I.V. is attributable to the mechanical and thermal degradation which the resin undergoes, in extrusion or spinning apparatus, during its conversion to fibers.

EXAMPLES 25 – 26

In each of Examples 25 and 26, 70 grams of poly(tetramethylene terephthalate) having an I.V. of 0.8 and 30 grams of poly(tetramethylene isophthalate/azelate) having an I.V. of 0.75 were charged to a glass reaction tube approximately 35 millimeters long, having an inside diameter of 38 millimeters and equipped with a side arm, nitrogen gas inlet tube and stainless steel stirrer. The polyester mixture in Example 25 was melted at 280° C. under a nitrogen atmosphere with constant stirring. Once the polyester mixture was completely melted, 1.5 parts by weight of the twice recrystallized, high melting TBP prepared in Example 1 per 100 parts by weight of polyester were added and the reaction mixture stirred for five minutes. The I.V. of the resulting product was 0.98.

The polyester mixture in Example 26 was also melted at 280° C. with constant stirring, but under vacuum. Again, once the polyester mixture was completely melted, 1.5 parts by weight of the twice recrystallized TBP prepared in Example 1 per 100 parts by weight of polyester were added to the melt and stirred for 5 minutes. The I.V. of the resulting product was 1.05.

The utility of the new high melting TBP was shown above employing poly(ethylene terephthalate) and a mixture of poly(tetramethylene terephthalate) and poly(tetramethylene isophthalate/azelate). The new high melting TBP can be also be employed in combination with other polyesters and copolyesters derived from various other dicarboxylic acids or lower alkyl esters thereof with various other glycols employing any of the well known polyester forming processes. Representative examples of other useful dicarboxylic acids include aromatic dicarboxylic acids such as isophthalic acid, 2,6- and 2,7-naphthanoic acid, p,p'-diphenyl dicarboxylic acid and the like; cycloaliphatic dicarboxylic acids such as hexahydroterephthalic acid and the like and aliphatic dicarboxylic acids such as adipic acid, suberic acid, azelaic acid, sebacic acid and the like. Mixtures of these acids can also be employed. Representative examples of the $C_1$ to $C_4$ alkyl esters of the above acids include the dimethyl, diethyl, dipropyl, diisopropyl, dibutyl and diisobutyl esters or mixtures thereof. Finally, in addition to ethylene glycol, glycols of the series $HO(CH_2)_nOH$ wherein n is an integer from 2 to 10, cycloaliphatic glycols and aromatic glycols can be used, examples of which include proplene glycol, tetramethylene glycol, neopentyl glycol, hexamethylene glycol, decamethylene glycol, cyclohexane dimethanol, di-β-hydroxyethoxy benzene and the like. Mixtures of these various glycols can also be employed. Because of its commercial significance, however, poly(ethylene terephthalate) prepared from either terephthalic acid or dimethyl terephthalate and ethylene glycol is the preferred polyester for use with the above described new high melting TBP.

The maximum molecular weight increase which can be achieved through the use of the high melting TBP material is dependent on the number of mols of polymerizing polyester or polyester resin and on the hydroxyl end group concentration therein. To achieve the maximum molecular weight increase $nz/2$ mols of the high melting TBP are required, where $n$ is the number of mols of polymerizing polyester or polyester resin and $x$ is the number of hydroxyl end groups present in each molecule of polyester. However, the high melting TBP can also be employed in varying amounts to achieve any molecular weight increase desired or to prevent any molecular weight decrease, with the actual amount employed being dependent on the purpose for which the high melting TBP is being employed, the intrinsic viscosity of the polymerizing polyester or polyester resin at the time of addition and on the ultimate molecular weight desired.

In general, the amount of the high melting TBP will range from about 0.01 to about 25.0 parts by weight per 100 parts by weight of either the original dicarboxylic acid or lower alkyl ester thereof when the TBP is added to a polymerizing melt of a polyester or the polyester resin when the TBP is added to remelted polyester resin, solid state polymerizing polyester or to polyester feed resin during the extrusion or spinning thereof into fiber. Specifically, when adding the high melting TBP to a melt polymerizing polyester of at least 0.2 I.V., the amount of the TBP will range from 1.0 to 20.0 parts by weight per 100 parts by weight of the starting dicarboxylic acid or lower alkyl ester thereof. These amounts provide for increased polymerization rates and the attainment polyesters having higher molecular weight in shorter than normal process times. When adding the high melting TBP to a melt polymerizing polyester of at least 0.6 I.V. the amount added will range from 0.1 to 5.0 parts by weight per 100 parts by weight of the starting dicarboxylic acid or lower alkyl ester thereof to provide polyesters of even higher molecular weight. The amount of high melting TBP employed, when added to 0.6 I.V. polyester granules or chips for subsequent melt or solid state polymerization or spinning, will also range from 0.1 to 5.0 parts by weight but will, in this instance, be based on 100 parts by weight of the polyester resin. Finally, when the high melting TBP is added to fiber forming polyester resin, having an I.V. of at least 0.8, the amount employed, depending on whether the objective is to produce a fiber having the same or higher I.V. than the starting resin, will range from 0.01 to 3.0 parts by weight per 100 parts by weight of the polyester resin. Addition of the high melting TBP to fiber forming polyester can be carried out either prior to or simultaneously with the addition of the polyester resin to the extrusion or spinning apparatus. Either method will provide the desired results.

While certain representative embodiments and details have been shown for the purpose of illustrating the invention it will be apparent to those skilled in this art that various changes and modifications may be made therein without departing from the spirit or scope of the invention.

What I claim is:

1. In a process for preparing high molecular weight linear polyesters of an aromatic dicarboxylic acid selected from the group consisting of terephthalic acid, isophthalic acid, 2,6-naphthoic acid, 2,7-naphthlic acid and p,p'-diphenyl dicarboxylic acid and copolyesters of at least one of said acids and a second acid by melt polymerizing the reaction product of the esterification or transesterification of the dicarboxylic acid or lower alkyl ester thereof with a glycol of the series $HO(CH_2)_nOH$ where $n$ is an integer ranging from 2 to 10 the improvement which comprises adding to the polymerizing product, when the intrinsic viscosity of said polymerizing product is at least 0.2, from 1.0 to 20.0 parts by weight of N,N'-terephthaloyl bis-phthalimide, having a melting point of at least 330° C., per 100 parts by weight of the dicarboxylic acid or lower alkyl ester thereof and reacting it with said polymerizing product to form a high molecular weight product.

2. The improvement of claim 1 wherein the N,N'-terephthaloyl bis-phthalimide is added to the polymerizing product of the transesterification reaction of dimethyl terephthalate with ethylene glycol.

3. In a process for preparing high molecular weight linear polyester and copolyesters having an intrinsic viscosity of at least 0.6 the improvement which comprises adding to a polyester or copolyester from 0.1 to 5.0 parts by weight of N,N-terephthaloyl bis-phthalimide, having a melting point of at least 330° C., per 100 parts by weight of said polyester or copolyester and reacting it with the polyester or copolyester.

4. The improvement of claim 3 wherein the polyester is poly(ethylene terephthalate).

5. In a process for preparing high molecular weight polyester and copolyester fibers from polyester and copolyester resins by melt extrusion of resins, having an intrinsic viscosity of at least 0.60 as measured in a 60/40 phenol/tetrachloroethane mixed solvent at 30° C. the improvement which comprises adding to a polyester or copolyester from 0.1 to 5.0 parts by weight of N,N'-terephthaloyl bis-phthalimide, having a melting point of at least 330° C., per 100 parts by weight of said polyester or copolyester and reacting it with the polyester or copolyester.

6. The improvement of claim 5 wherein the polyester resin is poly(ethylene terephthalate).